United States Patent [19]

Zehner et al.

[11] Patent Number: 5,295,986

[45] Date of Patent: Mar. 22, 1994

[54] NEWBORN'S GROWTH ADJUSTABLE ABSORBENT DIAPER HAVING VARIABLE OVERLAPPING AND NON-OVERLAPPING EARS

[75] Inventors: Georgia L. Zehner, Larsen; Paulette M. Rosch, Appleton; Thomas W. Odorzynski, Green Bay; Bruce M. Siebers, Appleton; Timothy J. Blenke, Neenah, all of Wis.

[73] Assignee: Kimberly-Clark Corporation, Neenah, Wis.

[21] Appl. No.: 868,915

[22] Filed: Apr. 15, 1992

Related U.S. Application Data

[62] Division of Ser. No. 757,789, Sep. 11, 1991.

[51] Int. Cl.$^5$ .................. A61F 13/15; A61F 13/20
[52] U.S. Cl. ................ 604/385.1; 604/358; 604/369; 604/370; 604/385.2; 604/386; 604/391
[58] Field of Search ............ 604/358, 385.1, 385.2, 604/386, 390-392, 367, 369, 370

[56] References Cited

U.S. PATENT DOCUMENTS

| | | | |
|---|---|---|---|
| B1 3,860,003 | 4/1989 | Buell . | |
| B1 4,636,207 | 11/1989 | Buell . | |
| 3,016,599 | 1/1962 | Perry | 28/78 |
| 3,523,536 | 8/1970 | Ruffo . | |
| 3,572,342 | 3/1971 | Lindquist et al. . | |
| 3,595,235 | 7/1971 | Jespersen . | |
| 3,612,055 | 10/1971 | Mesek et al. . | |
| 3,618,608 | 11/1971 | Brink | 604/391 |
| 3,663,348 | 5/1972 | Liloia et al. | 161/116 |
| 3,665,921 | 5/1972 | Stumpf . | |
| 3,730,184 | 5/1973 | Mesek . | |
| 3,768,480 | 10/1973 | Mesek et al. . | |
| 3,777,758 | 12/1973 | Mesek . | |
| 3,779,246 | 12/1973 | Mesek et al. . | |
| 3,837,343 | 9/1974 | Mesek . | |
| 3,987,792 | 10/1976 | Hernandez et al. . | |
| 4,077,410 | 3/1978 | Butterworth et al. . | |
| 4,118,531 | 10/1978 | Hauser | 428/224 |
| 4,216,772 | 8/1980 | Tsuchiya et al. . | |
| 4,230,113 | 10/1980 | Mehta . | |
| 4,300,563 | 11/1981 | Brookfield | 604/385.1 |
| 4,304,234 | 12/1981 | Hartmann . | |
| 4,338,371 | 7/1982 | Dawn et al. . | |
| 4,352,355 | 10/1982 | Mesek et al. . | |
| 4,372,312 | 2/1983 | Fendler et al. . | |
| 4,374,888 | 2/1983 | Bornslaeger | 428/198 |
| 4,388,075 | 6/1983 | Mesek et al. . | |
| 4,397,645 | 8/1983 | Buell . | |
| 4,413,032 | 11/1983 | Hartmann et al. | 428/288 |
| 4,421,813 | 12/1983 | Athey | 428/195 |
| 4,430,086 | 2/1984 | Repke . | |

(List continued on next page.)

FOREIGN PATENT DOCUMENTS

| | | |
|---|---|---|
| 0070163 | 1/1983 | European Pat. Off. . |
| 0070164 | 1/1983 | European Pat. Off. . |
| 0108637 | 5/1984 | European Pat. Off. . |
| 0174775 | 3/1986 | European Pat. Off. . |
| 0317058A1 | 5/1989 | European Pat. Off. . |
| 0377212A2 | 7/1990 | European Pat. Off. . |
| 0396050A2 | 11/1990 | European Pat. Off. . |
| 0403832A1 | 12/1990 | European Pat. Off. . |
| 0443082 | 8/1991 | European Pat. Off. ......... 604/385.2 |
| 61-2854 | 1/1986 | Japan . |
| 63-131710 | 8/1988 | Japan . |
| WO86/05661 | 9/1985 | PCT Int'l Appl. . |
| 2209672A | 5/1989 | United Kingdom . |
| WO84/04242 | 11/1984 | World Int. Prop. O. . |

Primary Examiner—Randall L. Green
Assistant Examiner—P. Zuttarelli
Attorney, Agent, or Firm—Douglas L. Miller; John R. Schenian

[57] ABSTRACT

A growth adjustable diaper for newborn babies is adjustable in length by use of a foldable absorbent panel at the front edge of the diaper, and is adjustable about the waist of the baby by means of ear members that can overlap and attach to each other or not overlap and attach to the front section of the diaper. Cushion barriers are provided at the crotch section and back waist edge to protect the newborn's sensitive, tender skin.

47 Claims, 6 Drawing Sheets

U.S. PATENT DOCUMENTS

| | | | |
|---|---|---|---|
| 4,468,428 | 8/1984 | Early et al. | 428/221 |
| 4,475,912 | 10/1984 | Coates . | |
| 4,500,384 | 2/1985 | Tomioka et al. | 156/290 |
| 4,548,604 | 10/1985 | Ellsworth | 604/399 |
| 4,552,603 | 11/1985 | Harris, Jr. et al. | 156/167 |
| 4,573,988 | 3/1986 | Pieniak et al. | 604/379 |
| 4,578,414 | 3/1986 | Sawyer et al. | 524/310 |
| 4,610,682 | 9/1986 | Kopp . | |
| 4,626,305 | 12/1986 | Suzuki et al. . | |
| 4,639,949 | 2/1987 | Ales et al. . | |
| 4,642,819 | 2/1987 | Ales et al. . | |
| 4,646,362 | 3/1987 | Heran et al. . | |
| 4,657,539 | 4/1987 | Hasse | 604/385.2 |
| 4,661,102 | 4/1987 | Shikata et al. . | |
| 4,670,011 | 6/1987 | Mesek | 604/378 |
| 4,675,015 | 6/1987 | Brown . | |
| 4,681,581 | 7/1987 | Coates | 604/391 |
| 4,687,477 | 8/1987 | Suzuki et al. . | |
| 4,695,278 | 9/1987 | Lawson | 604/385.2 |
| 4,704,112 | 11/1987 | Suzuki et al. | 604/378 |
| 4,704,116 | 11/1987 | Enloe . | |
| 4,714,647 | 12/1987 | Shipp, Jr. et al. | 428/212 |
| 4,728,326 | 3/1988 | Gilles . | |
| 4,732,809 | 3/1988 | Harris, Jr. et al. | 428/373 |
| 4,738,677 | 4/1988 | Foreman . | |
| 4,743,246 | 5/1988 | Lawson . | |
| 4,753,646 | 6/1988 | Enloe | 604/385 |
| 4,769,023 | 9/1988 | Goebel et al. | 604/385 |
| 4,773,906 | 9/1988 | Krushel . | |
| 4,795,452 | 1/1989 | Blaney et al. . | |
| 4,795,454 | 1/1989 | Dragoo . | |
| 4,798,603 | 1/1989 | Meyer et al. | 604/378 |
| 4,801,298 | 1/1989 | Sorenson et al. | 604/384 |
| 4,822,435 | 4/1989 | Igaue et al. . | |
| 4,830,904 | 5/1989 | Gessner et al. | 428/219 |
| 4,834,740 | 5/1989 | Suzuki et al. . | |
| 4,834,741 | 5/1989 | Sabee | 604/385 |
| 4,846,823 | 7/1989 | Enloe . | |
| 4,857,067 | 8/1989 | Wood et al. . | |
| 4,861,652 | 8/1989 | Lippert et al. . | |
| 4,880,420 | 11/1989 | Pomparelli . | |
| 4,883,480 | 11/1989 | Huffman et al. . | |
| 4,883,707 | 11/1989 | Newkirk | 428/219 |
| 4,892,528 | 1/1990 | Suzuki et al. . | |
| 4,895,568 | 1/1990 | Enloe | 604/385.2 |
| 4,904,251 | 2/1990 | Igaue et al. . | |
| 4,906,243 | 3/1990 | Dravland | 604/394 |
| 4,909,803 | 3/1990 | Aziz et al. . | |
| 4,916,005 | 4/1990 | Lippert et al. . | |
| 4,917,696 | 4/1990 | De Jonckheere . | |
| 4,923,454 | 5/1990 | Seymour et al. | 604/368 |
| 4,936,840 | 6/1990 | Proxmire . | |
| 4,938,753 | 7/1990 | Van Gompel et al. . | |
| 4,938,754 | 7/1990 | Mesek . | |
| 4,938,757 | 7/1990 | Van Gompel et al. . | |
| 4,940,464 | 7/1990 | Van Gompel et al. . | |
| 4,973,326 | 11/1990 | Wood et al. . | |
| 4,978,570 | 12/1990 | Heyn et al. . | |
| 4,981,480 | 1/1991 | Gaudet et al. . | |
| 4,988,344 | 1/1991 | Reising et al. . | |
| 4,988,346 | 1/1991 | Pfefferkorn . | |
| 4,988,560 | 1/1991 | Meyer et al. . | |
| 4,994,054 | 2/1991 | Pigneul et al. . | |
| 5,019,073 | 5/1991 | Roessler et al. . | |
| 5,026,364 | 6/1991 | Robertson | 604/385.2 |
| 5,064,421 | 11/1991 | Tracy | 604/386 |
| 5,100,399 | 3/1992 | Janson et al. | 604/385.1 |
| 5,112,326 | 5/1992 | Quadrini | 604/391 |

NEWBORN'S GROWTH ADJUSTABLE ABSORBENT DIAPER HAVING VARIABLE OVERLAPPING AND NON-OVERLAPPING EARS

This is a divisional application of copending application Ser. No. 07/757,789, filed on Sep. 11, 1991.

BACKGROUND OF THE INVENTION

This invention pertains to a disposable article, and more particularly to a disposable absorbent article that is adjustable in length and attachment to accommodate the relatively fast growth of a newborn baby.

Currently, disposable absorbent articles find widespread use in infant and child care, and have generally replaced reusable cloth absorbent articles. A typical disposable absorbent article generally comprises a composite structure including a topsheet, a backsheet, and an absorbent between the topsheet and backsheet. These articles usually include some type of fastening system for fitting the article onto the wearer.

Although current disposable baby diapers have been generally accepted by the public, these diapers still have need of improvement in specific areas. For example, mothers of newborns between the age of zero and generally about four months are aware of the irritation that current disposable diapers cause with the umbilical cord during the first month of the newborn's existence. Naturally, any irritation of the umbilical cord is a discomfort to the newborn and of anxious concern to the mother. Another serious concern to mothers is the tenderness of the newborn's skin and thus its sensitivity to even slight pressures or rubbing actions that can cause irritation and red marking. With current diapers, this irritation or pressure is caused by leg elastics that press the diaper tightly against the newborn's skin to prevent urine leakage. It also can occur at the waist area where the back ears of the diaper are adhesively attached tightly to the front section of the diaper. Thus, it can be appreciated that current diapers do not provide an optimum absorbent article for newborn babies.

In addition to concerns for the newborn's healing umbilical cord area and tender, sensitive skin is the relatively rapid growth of the newborn between the time when he or she is born to approximately the age of four months. During this time the newborn will grow in length and weight from about six pounds to about fifteen pounds, thus posing a problem to the mother since the diaper the mother was first using was sized for the baby at birth, while the next size diaper may not be appropriate to a newborn during this rapid growth stage. Thus, it would be desirable to have a diaper exclusively designed for a newborn between the age of zero and about four months that provides adjustability in size to accommodate this rapid growth.

SUMMARY OF THE INVENTION

In one form of the invention, there is provided a growth adjustable absorbent article comprising a backsheet including a front section, a back section, and an intermediate crotch section, and a main absorbent body disposed on at least the intermediate crotch section. A foldable panel is disposed on the front section between the main absorbent body and the front edge of the front section. This foldable panel is moveable between a first position in which it is substantially coplanar with the main absorbent body and a second position in which the foldable panel is folded inwardly upon the main absorbent body, thereby providing adjustability to the article.

BRIEF DESCRIPTION OF THE DRAWINGS

The above-mentioned and other features of the present invention, and the manner of attaining them, will become more apparent and the invention itself will be better understood by reference to the following description of the invention, taken in conjunction with the accompanying drawings, wherein.

DESCRIPTION OF A PREFERRED EMBODIMENT

Referring to FIGS. 1–4, and 9, a preferred embodiment of the present invention is illustrated as diaper 2 comprising front section 4 having front edge 6, back section 8 having back edge 10, and intermediate crotch section 12. Back section 8 further comprises a pair of ear members 14, 16 attached to or integral with back section 8. Generally, ear members 14, 16 will be integral to back section 8.

Figure 3:
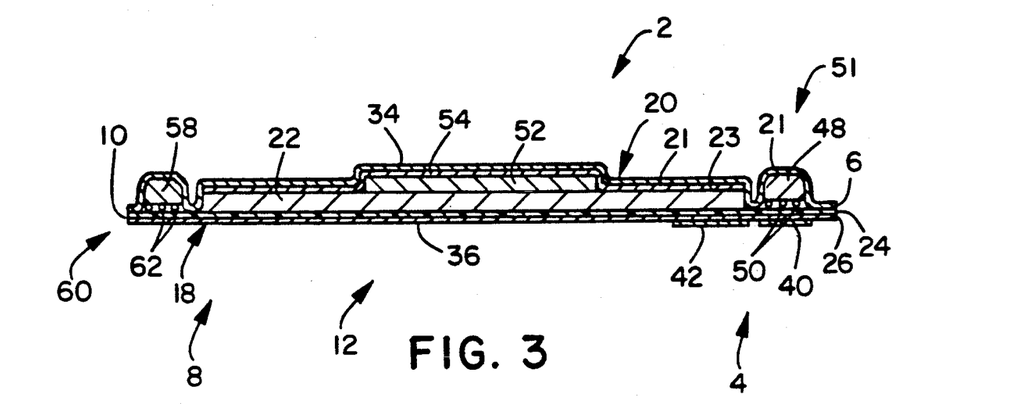
FIG. 3 is a cross-section of the embodiment in FIG. 1 taken along line 3—3 and viewed in the direction of the arrows.
Figure 4:
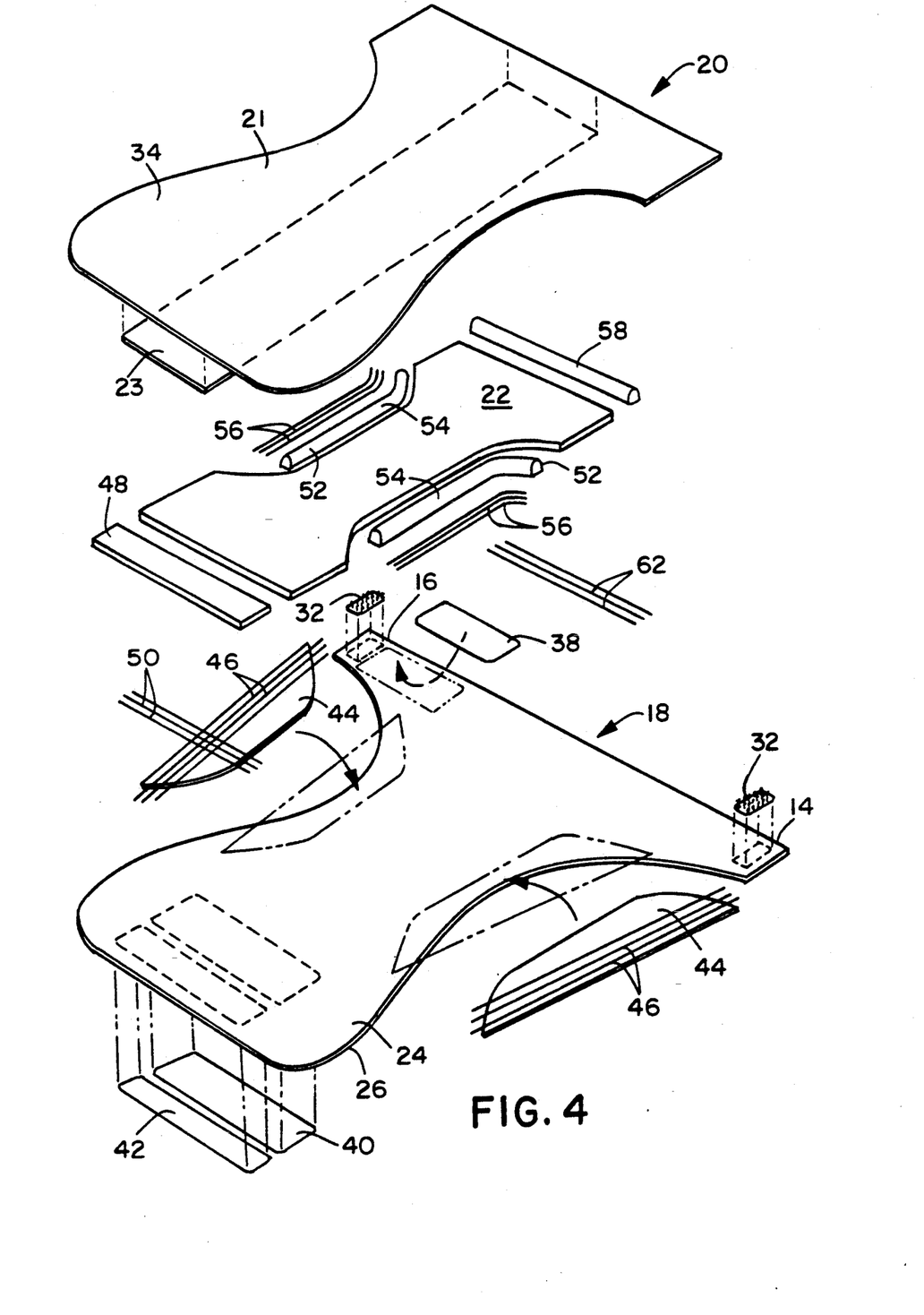
FIG. 4 is an exploded perspective of the embodiment in FIG. 1.

Diaper 2 further comprises backsheet 18 and topsheet 20 having positioned therebetween main absorbent body 22. Backsheet 18 and topsheet 20 may be of the same size and shape in which ear members 14, 16 would be formed by extensions of backsheet 18 and topsheet 20. If desired, topsheet 20 need not be coincident with backsheet 18, but it is preferred that both backsheet 18 and topsheet 20 have a length and width greater than that of main absorbent body 22 to allow their peripheries to be attached in any suitable manner. As illustrated in FIG. 3, main absorbent body 22 does not extend the full length of diaper 2, but is positioned at least at intermediate crotch section 12.

Preferably, backsheet 18 has both cloth-like and liquid-impermeable properties. The cloth-like properties are naturally preferred on the outermost surface of backsheet 18 to give a natural cloth feel to diaper 2 for both the newborn and mother or caretaker. This is in contrast to current diapers that use only a polymeric film material as the backsheet that has a plastic touch or feel. One means of providing backsheet 18 with both cloth-like and liquid-impermeable properties is to construct it of two plies, a liquid-impermeable inner ply 24, which may also be breathable or non-breathable to vapor, and a cloth-like outer ply 26. Inner ply 24 can be a thin film of liquid-impermeable material that is extruded onto a spunbond material as outer ply 26.

Figure 5:
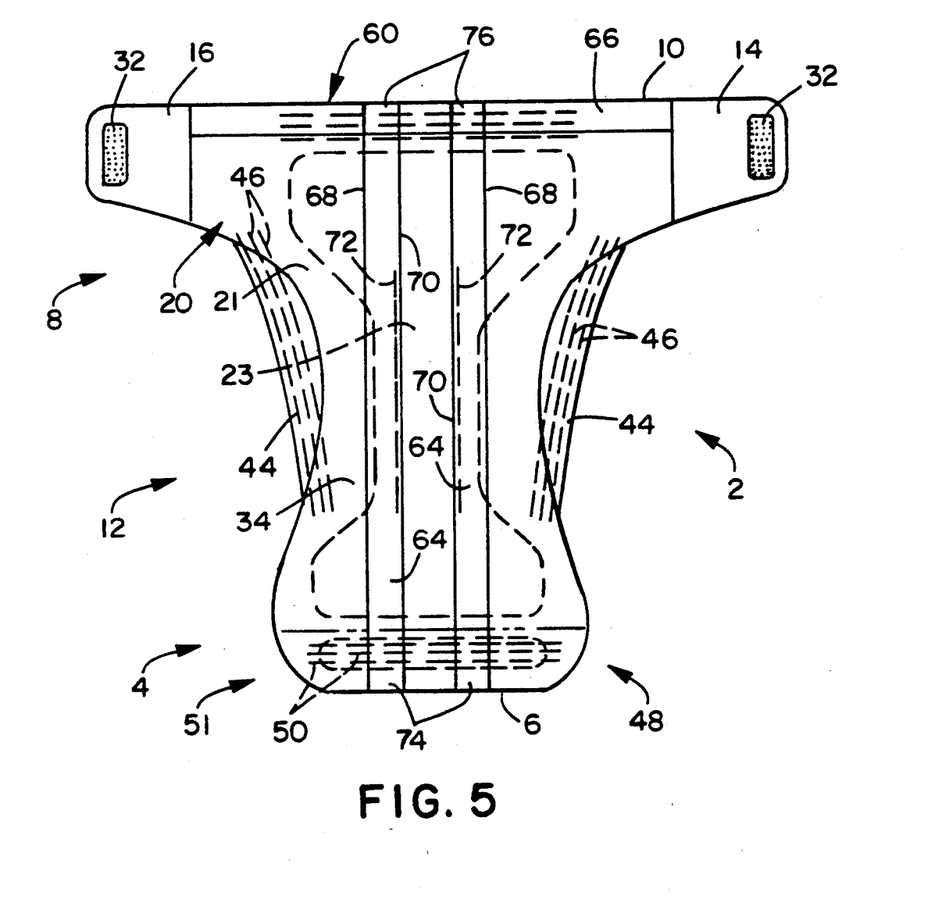
FIG. 5 is a top plan view of the bodyside of a modification to the embodiment in FIG. 1.

Topsheet 20 is permeable to liquids, such as urine and, in one of the unique aspects of the present invention, has a very soft feel or texture that is highly desirable for the sensitive, tender skin of a newborn. One preferred means of providing topsheet 20 with this extremely soft feel or texture is to construct it of a matrix of fibers in which all or at least some of the fibers are bicomponent fibers. These bicomponent fibers can be side-by-side or sheath-core construction. A more detailed description of topsheet 20 is provided hereafter. In one preferred embodiment, topsheet 20 is a two-layer composite comprising liner layer 21 made of bicomponent fibers and surge layer 23 made of a mixture of bicomponent fibers and other fibers. Liner layer 21 and surge layer 23 can be placed on top of each other without any additional step of bonding the two layers together, or liner layer 21 and surge layer 23 may be placed together followed by a bonding or joining step that integrates layers 21, 23 together to form topsheet 20. Surge layer 23 preferably is narrower than liner layer 21 and centered between cushion barriers 52 or containment flaps 64 (FIG. 5). Surge layer 23 preferably is between liner layer 21 and absorbent body 22.

Ear members 14, 16 have respective hook surfaces 32 attached near their ends on inner surface 34 of diaper 2. Each hook surface 32 comprises a plurality of hook members (not shown) that are compatible with a plurality of loop members to be described hereafter.

Figure 1:
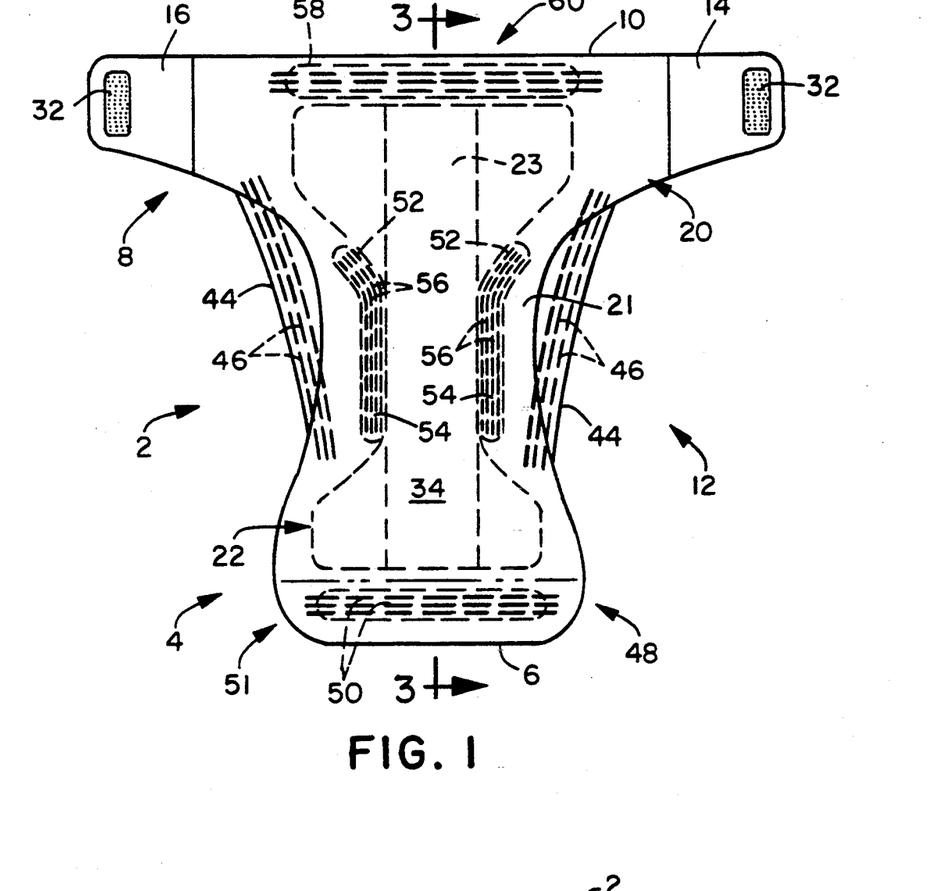
FIG. 1 is a top plan view of the bodyside of a preferred embodiment of the present invention when laid flat.
Figure 2:
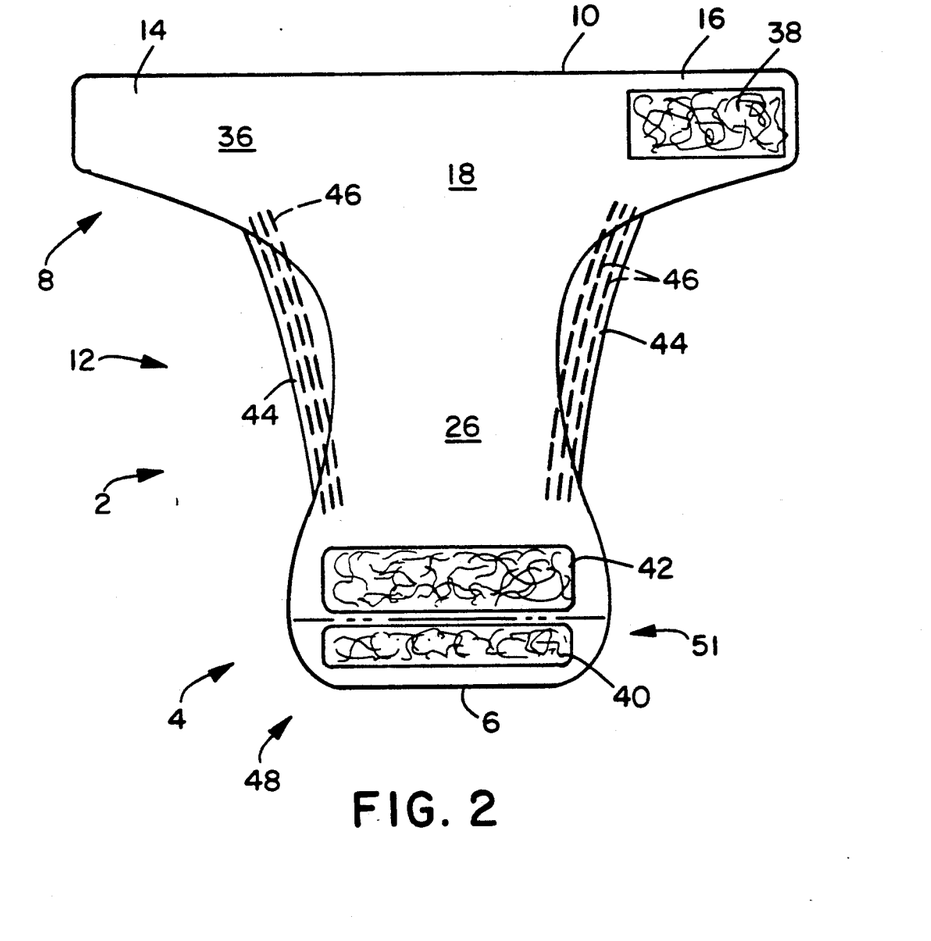
FIG. 2 is a top plan view of the backside of the embodiment in FIG. I when laid flat.

Diaper 2 further includes outer surface 36 on which is placed three loop surfaces 38, 40, 42. Loop surface 38 is attached to either or both ear member 14 or ear member 16, and in FIG. 3 is illustrated as being attached to ear member 16 on outer surface 36. Loop surfaces 40, 42 are attached to outer surface 36 at front section 4. As illustrated in FIGS. 2 and 3, loop surface 40 is near front edge 6 and loop surface 42 is spaced slightly inwardly of loop surface 40. If desired, loop surfaces 40, 42 can be one single loop surface. Loop surfaces 38, 40, 42 respectively comprise a plurality of loop members (not shown) that are compatible with the plurality of hook members on hook surfaces 32.

A pair of elasticized leg cuffs 44 are positioned on respective longitudinal sides of diaper 2, and preferably are attached between backsheet 18 and topsheet 20. Leg cuffs 44 can be liquid permeable or liquid impermeable, and are preferably elasticized by a plurality of elastic threads 46. Leg cuffs 44 are preferably a two-ply composite in which the outermost ply is liquid impermeable and the innermost ply is liquid permeable. In this design, the outermost ply can be made of the same material as backsheet 18 and the innermost ply can be made of the same material as liner layer 21. If it is desired that leg cuffs 44 be liquid permeable, both plies can be made of the same or different permeable materials.

Figure 6:
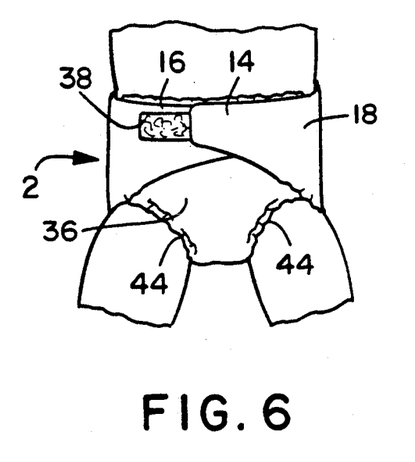
FIG. 6 is a view of the embodiment in FIG. 1 on a newborn baby with the foldable absorbent panel folded inwardly and the ears overlapping.
Figure 7:
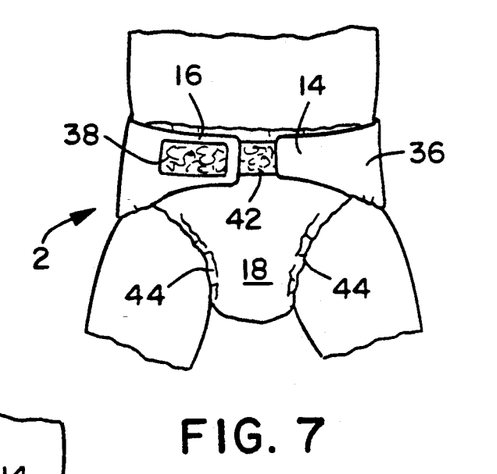
FIG. 7 is similar to FIG. 6 except that the ears do not overlap.

In addition to main absorbent body 22, diaper 2 further comprises foldable absorbent panel 48 between main absorbent body 22 and front edge 6. As with main absorbent body 22, foldable absorbent panel 48 is positioned between backsheet 18 and topsheet 20. Foldable absorbent panel 48 can be made of the same absorbent material as main absorbent body 22 and, as illustrated in FIG. 3, is spaced from main absorbent body 22. If desired, main absorbent body 22 and foldable absorbent panel 48 can be integral and yet separately identified by embossing, creasing, aperturing, or the like so as to permit foldable absorbent panel 48 to fold inwardly as indicated in FIGS. 6 and 7. It should also be noted that loop surface 40 is foldable inwardly with absorbent panel 48, as are those portions of backsheet 18 and topsheet 20 that overlie absorbent panel 48. If desired, foldable panel 48 can be made of a non-absorbent material preferably having liquid damming or barrier characteristics.

In order to provide elasticity to the front waist portion of diaper 2, which is that portion of front section 4 adjacent front edge 6, a plurality of elastic threads 50 are joined between absorbent panel 48 and backsheet 18. Elastic threads 50 can be first stretched and then adhered to either backsheet 18 or panel 48 or both. Alternatively, elastic threads 50 can be made of a heat elasticizable material in which they are joined in a relaxed condition and then heated to become elastic so as to gather backsheet 18. If desired, elastic threads 50 can be joined to a separate layer of material to form an elastic composite and then joined between backsheet 18 and absorbent panel 48.

One unique aspect of the present invention that addresses the sensitivity and tenderness of a newborn's skin are the presence of cushion barriers that assist in preventing leakage, while minimizing any irritation or red marking of the skin. A pair of curved crotch cushion barriers 52 are provided on opposite sides of main absorbent body 22 at least in the area of intermediate crotch section 12. Each crotch cushion barrier is spaced slightly apart from main absorbent body 22 so that they may easily flex or fold to match the newborn's body shape. Each cushion barrier 52 has a top surface 54 that extends upwardly beyond main absorbent body 22 in order to provide a cup-like shape and more importantly to seal gently against the newborn's skin. Each cushion barrier 52 is generally elongate in shape, and may be cylindrical, rectangular, oval, or the like in its transverse, cross-sectional shape. Cushion barriers 52 can be made of the same material as main absorbent body 22, or can be made of other material that is not absorbent but resilient to provide a damming effect to body wastes and a gentle seal against the skin. If desired, an elastic member 56 can be provided to each cushion barrier 52 between the respective cushion barrier 52 and backsheet 18. Elastic members 56 serve to urge cushion barriers 52 against the newborn's skin in a gentle, soft manner. Elastic members 56 can be of the same construction and of the same materials as described for elasticizing foldable absorbent panel 48 with elastic threads 50. Elastic members 56 are preferably elongate members similar in length and width to their respective cushion barriers 52. The height with which top surfaces 54 extend upwardly beyond the top surface of main absorbent body 22 will vary depending upon the absorbent materials used, the size and shape of diaper 2, and the like. Cushion barriers 52 are preferably positioned between backsheet 18 and liner layer 21, but may be on top of liner layer 21.

Although cushion barriers 52 have been described as being slightly spaced apart from the longitudinal sides of main absorbent body 22, they may be placed further apart from absorbent body 22 by as much as 2 centimeters, or may be positioned on top of main absorbent body 22 near its respective longitudinal sides.

Back section 8 includes back waist cushion barrier 58 positioned between main absorbent body 22 and back edge 10. Preferably, back waist cushion barrier 58 is sandwiched between backsheet 18 and liner layer 21, but may be on the top of liner layer 21. Back waist cushion barrier 58 can be made of the same materials as crotch cushion barriers 52, and includes a back waistband 60. Back waistband 60 can be constructed and made of the same materials as front waistband 51. Thus, back waistband 60 can comprise elastic threads 62 that are identical or similar to elastic threads 50 of front waistband 51. Back waist cushion barrier 58 serves both to provide a gentle cushion against the newborn's skin and to provide a waste barrier at the back of diaper 2. Back waist cushion barrier 58 is generally of the same width as main absorbent body 22 at back section 8, but naturally can be greater or lesser in width than absorbent body 22 as desired.

Referring to FIG. 5, diaper 2 has been modified to replace crotch cushion barriers 52 with a pair of containment flaps 64, and to replace back waist cushion barrier with waste containment flap 66. Containment flaps 64 can be made of the same material as liner layer 21, or may be made of other suitable material. Containment flaps 64 can be formed in generally one of two methods. One method is to make each containment flap 64 as an individual structural element and then attach it in any suitable manner to liner layer 21. In this method, each proximal edge 68 of a respective containment flap 64 is attached to liner layer 21. In another method, containment flaps 64 are made from liner layer 21 by essentially pleating liner layer 21 and then adhering proximal edges 30 together. In both methods, distal edges 70 include at least a single strand 72 of stretchable material that is attached in a stretched condition to distal edges 70. Front ends 74 and back ends 76 of containment flaps 64 are secured to liner layer 21. Upon relaxing or fitting diaper 2, elastic strands 72 cause edges 70 to extend upwardly from liner layer 21. As described, containment flaps 64 are located inwardly or inboard of leg cuffs 44, as are cushion barriers 52. A more detailed description of the construction of flaps 64 is contained in U.S. Pat. No. 4,704,116 to Enloe, the contents of which are incorporated by reference herein.

Waste containment flap 66 can be identical or similar to containment flaps 64, except that it is attached at back section 8 near back edge 10. Waste containment flap 66 can be constructed in the same manner as containment flaps 64 and can be made of the same materials. Both containment flaps 64 and waste containment flap 66 can be made of liquid impermeable or liquid permeable materials as described hereafter.

Referring to FIG. 6, diaper 2 is illustrated as it would appear at its shortest length of about 12 inches to about 13.75 inches on a newborn. Diaper 2 is fitted on a newborn in generally the same manner as current diapers, except for the following steps. Foldable absorbent panel 48 is folded inwardly so that the outer surfaces of foldable absorbent panel 48 and main absorbent body 22 are in mutually facing relationship. Folded with foldable absorbent panel 48 are loop surface 40 and front waistband 51. Loop surface 40 is made of a soft material that will not irritate the baby's skin. After this folding step, the newborn can be placed on diaper 2 and front section 4 is pulled between the legs and towards and against the front of the baby. Ear members 14, 16 are then wrapped around the waist of the newborn and positioned such that hook surface 32 of ear member 16 releasably engages loop surface 42, and hook surface 32 of ear member 14 engages loop surface 38 on ear member 16. This fastening of ear members 16 and 14 to loop surface 42 and loop surface 38, respectively, can be adjusted in order to snugly, but comfortably, fit diaper 2 to the newborn. In this folded form, diaper 2 is in its shortest length, and ear members 14, 16 overlap each other to accommodate the newborn's waistline which is at its smallest measurement at this point of the newborn's life.

Referring to FIG. 7, as the newborn begins to rapidly grow during the first several weeks or months after birth, diaper 2 can be adjusted as necessary to match this growth trend. Foldable absorbent panel 48 can remain folded inwardly, but ear members 14, 16 can be positioned on loop surface 42 in a non-overlapping manner as necessitated by the newborn's increasing waistline. In this intermediate size adjustment of diaper 2, hook surfaces 32 of both ear members 14, 16 are attached to loop surface 42.

Figure 8:
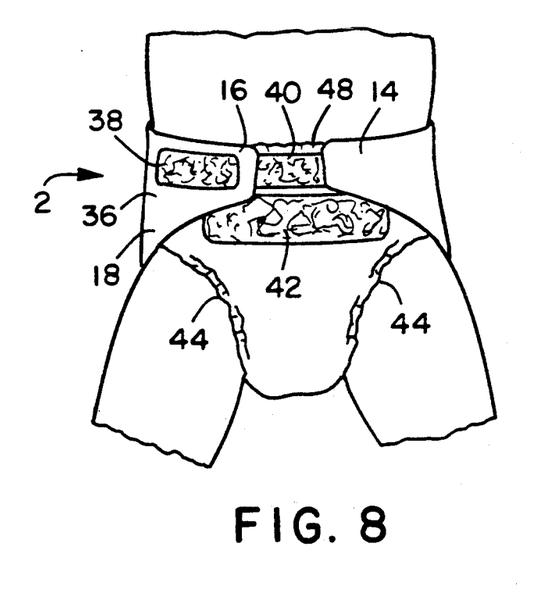
FIG. 8 is similar to FIG. 7 except that the foldable absorbent panel has been unfolded with the ears attached thereto.
Figure 9:
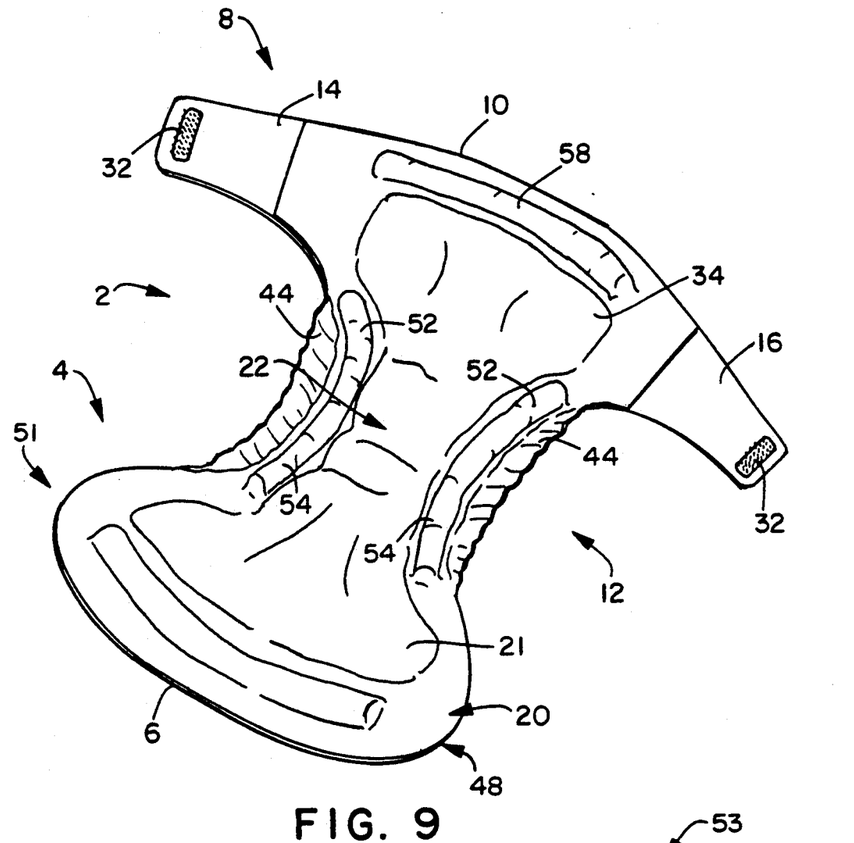
FIG. 9 is a perspective view of the embodiment in FIG. 1.

As the newborn continues to rapidly grow, diaper 2 continues to match this development in both the length and the width of the newborn. As illustrated in FIG. 8, to accommodate the growth in length, foldable absorbent panel 48 has been returned to a substantially coplanar position with main absorbent body 22 as indicated in FIG. 3 in order to provide maximum length of about 14 inches to about 15 inches to diaper 2, and ear members 14, 16 are now attached in a non-overlapping manner to loop surface 40 on foldable absorbent panel 48.

Figure 10:
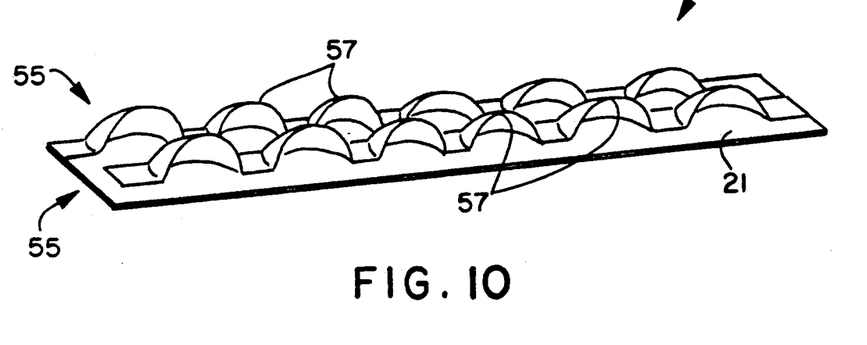
FIG. 10 is a perspective view of another cushion barrier.

Referring to FIG. 10, a modification to cushion barriers 52, 58 is illustrated as numeral 53. This modification includes at least one, and preferably two as illustrated, row 55 comprising a plurality of cup-like members 57 that receive and collect body wastes. Members 57 face inwardly toward a longitudinal centerline of diaper 2, and when there are two rows 55 the cup-like members 57 in one row 55 are staggered with members 57 of the other row 55. Members 57 can be liquid permeable or impermeable, and vapor permeable or impermeable. Generally, members 57 are made of a material that can be easily molded or formed to the desired shape and geometry. If desired, these rows 55 of cup-like members 57 also can be provided with cushion barriers 52 and would be positioned between respective cushion barriers 52 and leg cuffs 44.

Each cup-like member 57 comprises an inner edge, an outer edge, and side edges. The inner edge of the cup-like member 57 is positioned nearer to, or proximal to, the longitudinal centerline of the absorbent article than the outer edge which is positioned further away from, or distal to, the longitudinal centerline of the absorbent article. The inner edge is unattached to, and said outer edge and said side edges are attached to, said topsheet to form a pocket-like void that receives and collects body wastes.

Backsheet 18 is a two-ply composite in which the inner ply 24 is liquid impermeable and outer ply 26 liquid permeable. Preferably, inner ply 24 is a polypropylene film having a thickness of about 0.5 to about 1.0 mils, and outer ply 26 is spunbond polypropylene having a basis weight of about 0.3 to about 1.0 ounces per square yard; the polypropylene fibers being bilobal in shape, and having a denier of about 1.5 to about 4.0 dpf (denier per filament). Inner and outer piles 24, 26 can be joined in any suitable manner, such as by spray adhesive, lines of adhesive, dot bonding, thermal bonding, sonic bonding, extruding the film layer onto the spunbond layer, and the like. Backsheet 18 may be made of other materials that are liquid impermeable or treated to be so. Some examples are meltblown or film material made of polyethylene or polyolefin copolymers. Backsheet 18 may also be vapor permeable as well as liquid impermeable. Backsheet 18 generally will form the shape of diaper 2 and, as illustrated in the figures, is generally hourglass shape with ear members 14, 16 extending laterally outwardly. Other shapes are usable and will depend upon the types of materials used, their thicknesses, and the like.

Topsheet 20 is made of a liquid-permeable material and is preferably a two-layer composite. In a preferred embodiment, topsheet 20 is an integrated bonded carded web having a basis weight of about 1.5 osy (ounces per square yard). Liner layer 21 is made of a polyethylene/polyester bicomponent fiber having a basis weight of about 0.5 osy and a fiber denier of about 2.25 dpf. This type of bicomponent fiber can be purchased from BASF Corporation, Fibers Division, Enka, N.C. 28728. Surge layer 23 is preferably a fiber matrix having a basis weight of about 1.0 osy and comprising about 75 percent by weight polyester fibers having a denier of about 15 dpf and 25 percent by weight of a polyethylene/polypropylene bicomponent fiber. These fibers can be purchased from Chisso Corporation, PP Fiber Division, 6-32, Nakanoshima 3, Kits-Ku, Osaka-530, Japan. These two layers can be integrated by, for example, through-air bonding or infra-red bonding. Topsheet 20 preferably has a density of about 0.02 gcc (grams per cubic centimeter) and a bulk thickness of about 0.10 inches. This combination of layers and fibers provides an extremely soft, gentle surface for placement against the newborn's skin and is one of the unique features of the present invention. Although a preferred embodiment of topsheet 20, topsheet 20 can have a basis weight between 15 to about 102 gsm (grams per square meter), a density between about 0.01 to about 0.08 gcc, a fiber denier between about 1 to about 15 dpf, and fiber lengths between about 0.5 to about 2.0 inches in which the fibers may be crimped in a range of about 14 to about 22 crimps per inch.

Topsheet 20 can also be made of other liquid-permeable materials, such as spunbond webs of synthetic polymer filaments, a spunlace web, and the like. Topsheet 20 can have the same shape as backsheet 18, or may be smaller in length or width. However, it is preferred that topsheet 20 and backsheet 18 have peripheries that extend outwardly beyond main absorbent body 22 so that their peripheral portions can be adhered together, such as by lines of adhesive or sonic bonding, or a combination of both.

Main absorbent body 22 is preferably a mixture of pulp fluff and superabsorbent material in which the fluff is present in the amount of about 13.4 grams and the superabsorbent material is present in the amount of about 7.2 grams. A suitable superabsorbent material can be purchased from Hoechst Celanese, Super Absorbent Division, Portsmouth Technical Center, 3340 West Norfolk Road, Portsmouth, Va. 23703. Other superabsorbent material can be suitably used and examples include organic materials such as silica gels or organic compounds such as cross-linked polymers. The superabsorbent materials can be in various forms, such as particles, fibers, layers, and the like. The superabsorbent material and fluff can be uniformly blended, blended to have a Z-gradient, or the superabsorbent material can be layered or multi-layered within the fluff. Absorbent body 22 preferably has a surface area of about 41 square inches, a density of about 0.2 gcc, and a basis weight of about 778 gsm. Absorbent body 22 includes two layers of standard tissue wrap having a basis weight of about 22 gsm. The tissue wrap is adhesively sealed about the perimeter of absorbent body 22, or can be heat sealed if desired.

Foldable absorbent panel 48 can be made of the same identical materials as absorbent body 22 or from different suitable materials. For example, it may be preferred that foldable panel 48 not be absorbent and thus would be made of a non-absorbent material or of an absorbent material being enclosed within a liquid-impermeable layer.

Both main absorbent body 22 and absorbent panel 48 can be attached or joined to backsheet 18 in any suitable manner, such as by lines of adhesive.

Loop surfaces 38, 40, 42 are preferably made of a loop material purchasable from Guilford Mills, Inc., 6001 West Market Street, Greensboro, N.C., 27402, and identified as Guilford Loop Style No.s 18903 or 19902. The shape of each loop surface 38, 40, 42 is dependent upon the overall shape of diaper 2. As illustrated, loop surface 38 is rectangular, and loop surfaces 40, 42 are also rectangular and extend nearly the width of front section 4. Loop surfaces 38, 40, 42 can be attached to backsheet 18 by lines of adhesive, sonic bonding, or any other suitable means.

Hook surfaces 32 are preferably a hook material purchasable from Velcro USA, Manchester, N.H., and are identified as Hook HTH 708. Hook surfaces 32 are attached to ear members 14, 16 by lines of adhesive, sonic bonding, or the like.

The elastic material of which elastic threads 46, elastic threads 50, elastic threads 62, and elastic strands 72 are made is preferably Lycra.

Cushion barriers 52, 58 can be made of the same material as main absorbent body 22, or may be made of fluff fibers or synthetic fibers alone. If it desired that barriers 52, 58 not be absorbent, then they can be made of any suitable resilient material such as a foam material.

Although FIG. 5 illustrated cushion barriers 52, 58 being replaced by containment flaps 64, 66, the present invention contemplates other combinations of these elements. For example, diaper 2 may include crotch cushion barriers 52 with waste containment flaps 66, or back waist cushion barrier 58 with containment flaps 64.

While this invention has been described as having a preferred embodiment, it will be understood that it is capable of further modifications. This application is therefore intended to cover any variations, equivalents, uses or adaptations of the invention following the general principles thereof, and including such departures from the present disclosure as come within known or customary practice in the art to which this invention pertains and fall within the limits of the appended claims.

What is claimed is:

1. A growth adjustable absorbent article having a length, said article comprising:
    a backsheet including a front section having a front edge, a back section having a back edge, and an intermediate crotch section having opposite sides,
    a main absorbent body being disposed on at least said intermediate crotch section,
    a foldable absorbent panel being disposed on said front section between said main absorbent body and said front edge of said front section, said foldable absorbent panel being movable between a first position wherein said foldable absorbent panel is substantially coplanar with said main absorbent body and a second position wherein said foldable absorbent panel is folded inwardly upon said main absorbent body, whereby the length of said article is adjustable to accommodate the growth of a newborn baby.

a topsheet, and a crotch cushion barrier being disposed on each side of said crotch section, wherein said cushion barrier comprises at least one row of cup-like members, wherein each cup-like member comprises an inner edge, an outer edge, and side edges, wherein said inner edge is unattached to, and said outer edge and said side edges are attached to, said topsheet to form a pocket-like void, and wherein said cup-like members face inwardly towards a longitudinal centerline of the absorbent article.

2. The article of claim 1 further comprising an elastic member affixed to said front section.

3. The article of claim 1 further comprising a back waist cushion barrier positioned between said main absorbent body and said back edge.

4. The article of claim 1 wherein said cushion barrier is made of an absorbent material.

5. The article of claim 1 wherein said cushion barrier is made of non-absorbent material.

6. The article of claim 1 wherein said cushion barrier is liquid impermeable.

7. The article of claim 1 wherein said cushion barrier is liquid permeable.

8. The article of claim 1 wherein said cushion barrier is made of a foam material.

9. The article of claim 1 further comprising an elastic member between said cushion barrier and said backsheet.

10. The article of claim 1 further comprising a waist containment flap attached to said back section near said back edge.

11. The article of claim 1 further comprising a loop surface attached to an outer surface of said absorbent article at said front section, and a pair of ear members integral with said back section, each said ear member including a hook surface,
said hook surfaces being releasably engageable with said loop surface.

12. The article of claim 11 wherein one of said ear members further includes a loop panel attached to an outer surface of said absorbent article, said hook surface of said one ear member being releasably engageable with said loop surface,
said hook surface of said other ear member being releasably engageable with said loop panel on said one ear member.

13. The article of claim 12 wherein said loop surface comprises a foldable loop surface foldable with said foldable absorbent panel, and a loop surface positioned inwardly of said foldable loop surface,
said hook surface of said one ear member being releasably engageable with said loop surface positioned inwardly of said foldable surface when said foldable absorbent panel is in said folded second position,
said hook surface of said other ear member being releasably engageable with said loop panel on said one ear member.

14. The article of claim 11 wherein said loop surface comprises a foldable loop surface foldable with said foldable absorbent panel, and a loop surface on said backsheet positioned inwardly of said foldable loop surface.

15. The article of claim 14 wherein said hook surfaces are releasably engageable with both said loop surfaces.

16. The article of claim 14 wherein said hook surfaces are releasably engageable to one of said loop surfaces.

17. The article of claim 1 further comprising a topsheet comprising bicomponent fibers.

18. The article of claim 17 wherein said bicomponent fibers are sheath-core fibers.

19. The article of claim 17 wherein said bicomponent fibers are side-by-side fibers.

20. The article of claim 17 wherein said topsheet has a basis weight between about 15 to about 102 grams per square meter and a density between about 0.01 to about 0.08 grams per cubic centimeter.

21. The article of claim 17 wherein said fibers have a denier between about 1 to about 15 dpf, and a length between about 0.5 to about 2.0 inches.

22. The article of claim 17 wherein said fibers are crimped in a range of about 14 top about 22 crimps per inch.

23. A growth adjustable absorbent article, comprising:

a backsheet including a front section having a front edge, a back section having a back edge, and an intermediate crotch section having opposite sides, a main absorbent body being disposed on at least said intermediate crotch section, a foldable absorbent panel being disposed on said front section between said main absorbent body and said front edge, said foldable absorbent panel being movable between a first position wherein said foldable absorbent panel is substantially coplanar with said main absorbent body and a second position wherein said foldable absorbent panel is folded inwardly upon said main absorbent body, a pair of ear members integral with said back section, one of said ear members being releasably engageable with said front section, the other said ear member being positionable between a first position wherein said other ear member overlaps and is releasably engageable with said one ear member and a second position wherein said other ear member is spaced from said one ear member and is releasably engageably with said front section, a topsheet, and a crotch cushion barrier being disposed on each side of said crotch section, wherein said cushion barrier comprises at least one row of cup-like members, wherein each cup-like member comprises an inner edge, an outer edge, and side edges, wherein said inner edge is unattached to, and said outer edge and said side edges are attached to, said topsheet to form a pocket-like void, and wherein said cup-like members face inwardly towards a longitudinal centerline of the absorbent article.

24. The article of claim 23 wherein said other ear member is positionable at its said first position when said foldable absorbent panel is at its said second position.

25. The article of claim 23 wherein said other ear member is positionable at its said second position when said foldable absorbent panel is at its said first position.

26. The article of claim 23 further comprising a back waist cushion barrier positioned between said main absorbent body and said back edge.

27. The article of claim 23 further comprising a waist containment flap attached to said back section near said back edge.

28. The article of claim 23 further comprising a topsheet comprising bicomponent fibers.

29. The article of claim 28 wherein said bicomponent fibers are sheath-core fibers.

30. The article of claim 28 wherein said bicomponent fibers are side-by-side fibers.

31. The article of claim 28 wherein said topsheet has a basis weight between about 15 to about 102 grams per square meter and a density between about 0.01 to about 0.08 grams per cubic centimeter.

32. The article of claim 28 wherein said fibers have a denier between about 1 to about 15 dpf, and a length between about 0.5 to about 2.0 inches.

33. The article of claim 28 wherein said fibers are crimped in a range of about 14 to about 22 crimps per inch.

34. An absorbent article, said absorbent article comprising:
   a backsheet including a front section having a front edge, a back section having a back edge, and an intermediate crotch section having opposite sides,
   a liquid permeable top sheet,
   a main absorbent body being disposed on at least said intermediate crotch section and being positioned between said topsheet and said backsheet,
   a topsheet, and
   a crotch cushion barrier being disposed on each side of said crotch section, wherein said cushion barrier comprises at least one row of cup-like members, wherein each cup-like member comprises an inner edge, an outer edge, and side edges, wherein said inner edge is unattached to, and said outer edge and said side edges are attached to, said topsheet to form a pocket-like void, and wherein said cup-like members face inwardly towards a longitudinal centerline of the absorbent article.

35. The article of claim 34 further comprising a back waist cushion barrier positioned between said main absorbent body and said back edge.

36. The article of claim 34 wherein said cushion barrier is made of an absorbent material.

37. The article of claim 34 wherein said cushion barrier is made of non-absorbent material.

38. The article of claim 34 wherein said cushion barrier is liquid impermeable.

39. The article of claim 34 wherein said cushion barrier is liquid permeable.

40. The article of claim 34 wherein said cushion barrier is made of a foam material.

41. The article of claim 34 further comprising an elastic member between said cushion barrier and said backsheet.

42. The article of claim 34 wherein said topsheet comprises bicomponent fibers.

43. The article of claim 42 wherein said bicomponent fibers are sheath-core fibers.

44. The article of claim 42 wherein said bicomponent fibers are side-by-side fibers.

45. The article of claim 42 wherein said topsheet has a basis weight between about 15 to about 102 grams per square meter and a density between about 0.01 to about 0.08 grams per cubic centimeter.

46. The article of claim 42 wherein said fibers have a denier between about 1 to about 15 dpf, and a length between about 0.05 to about 2.0 inches.

47. The articles of claim 42 wherein said fibers are crimped in a range of about 14 to about 22 crimps per inch.

* * * * *